United States Patent [19]
Slater et al.

[11] Patent Number: 5,866,912
[45] Date of Patent: Feb. 2, 1999

[54] SYSTEM AND METHOD FOR MULTIPLE PARTICLE THERAPY

[75] Inventors: James M. Slater, Redlands; Daniel W. Miller, Yucaipa; Jon W. Slater, Redlands, all of Calif.

[73] Assignee: Loma Linda University Medical Center, Loma Linda, Calif.

[21] Appl. No.: 25,992

[22] Filed: Feb. 19, 1998

Related U.S. Application Data

[63] Continuation of Ser. No. 423,774, Apr. 18, 1995, abandoned.
[51] Int. Cl.$^6$ .............................. H01J 37/30; H05H 3/00
[52] U.S. Cl. ....................................... 250/492.1; 250/251
[58] Field of Search .................................. 250/306, 307, 250/492.1, 492.3, 251

[56] References Cited

U.S. PATENT DOCUMENTS

| | | | |
|---|---|---|---|
| 4,442,352 | 4/1984 | Brahme | 250/505.1 |
| 4,666,651 | 5/1987 | Barjon et al. | 376/108 |
| 4,672,212 | 6/1987 | Brahme | 250/251 |
| 4,870,287 | 9/1989 | Cole et al. | 250/492.3 |
| 4,905,267 | 2/1990 | Miller et al. | 128/653.1 |
| 4,992,746 | 2/1991 | Martin | 327/235 |
| 5,017,789 | 5/1991 | Young et al. | 250/396 ML |
| 5,017,882 | 5/1991 | Finlan | 328/234 |
| 5,039,057 | 8/1991 | Prechter et al. | 248/664 |
| 5,117,829 | 6/1992 | Miller et al. | 128/653.1 |
| 5,260,581 | 11/1993 | Lesyna et al. | 250/492.3 |

FOREIGN PATENT DOCUMENTS

| | | |
|---|---|---|
| 0033050 | 8/1981 | European Pat. Off. . |
| 0059668 | 9/1982 | European Pat. Off. . |
| 0060771 | 9/1982 | European Pat. Off. . |

*Primary Examiner*—Bruce Anderson
*Attorney, Agent, or Firm*—Knobbe, Martens, Olson & Bear, LLP

[57] ABSTRACT

A system for delivering two types of particles to a target within the body of a patient. A proton beam therapy system produces a beam of protons that is directed from a nozzle towards a target isocenter located within the body of a patient. The beam of protons can pass directly to the patient or pass through a neutron source comprised of a plate of neutron-rich material. Collisions between some of the protons and neutrons cause neutrons to be emitted from the material thereby generating a multiple particle beam comprised of both protons and neutrons. Preferably, the neutrons comprise only a small percent of the total particles in the beam. In the preferred embodiment, the neutron source is comprised of a plate of Beryllium that is interposed between the nozzle and the patient.

33 Claims, 2 Drawing Sheets

SYSTEM AND METHOD FOR MULTIPLE PARTICLE THERAPY

RELATED APPLICATIONS

This is a continuation of U.S. patent application Ser. No. 08/423,774, filed Apr. 18, 1995 abandoned.

BACKGROUND OF THE INVENTION

1. Field of the Invention

The present invention relates to a system for particle beam therapy and, in particular, concerns a system for producing a beam comprising multiple types of particles, including protons and neutrons, which are delivered to a target isocenter within the patient to be treated.

2. Description of the Related Art

Radiation therapy is used to treat, among other things, various forms of cancer. In particular, radiation therapy is often used to treat tumors and cancerous tissues within the body of a patient. Generally, radiation therapy involves directing a beam of sub-atomic particles at a region within the body of the patient containing the cancerous tissue. Ideally, when the sub-atomic particles contact the cancerous tissue, the energy of the sub-atomic particles destroys these cells or prevents these cells from reproducing or growing. Various types of sub-atomic particles are used in various forms of radiation therapy including, photons (X-rays), neutrons and protons. Each form of particle therapy has certain advantages and disadvantages.

For example, neutrons have a comparatively high Radio Biologic Effect (RBE), which is an empirically measured value indicative of the amount of damage to cells that is caused by the particle. Hence, neutrons can be very effective in destroying or damaging cancerous cells. However, it is generally very difficult to control a neutron beam so as to direct neutrons from a remote source into particular localized regions of a patient's body. Further, as neutrons travel through the body, they release energy at a generally constant rate along their path of travel. Neutrons deposit energy along their path and are also slowed significantly as a result of penetrating tissue. Neutrons have the unfortunate tendency to damage healthy tissue surrounding the tissue of interest, i.e., healthy tissue along the path of travel of the neutrons. Additionally, neutrons present a particular safety hazard in that they can penetrate deeply into almost any type of material including steel and concrete. Thus, if large quantities of neutrons are generated, radiation shielding becomes a significant problem.

In contrast, protons generally have a lower RBE. However, they are easier to control and exhibit a characteristic known as the Bragg peak whereby the energy released by a proton penetrating tissue rapidly increases when the proton slows to a threshold level. Consequently, by controlling the energy of the protons so that they slow down at the proper time, it is possible to cause most of their energy to be released in the proximity of the region of the cancerous cells. Protons are, therefore, very effective in destroying cancerous cells within the body of a patient while minimizing damage to surrounding cells.

While proton therapy can be very effective in some circumstances, there are sometimes cases where the RBE of a beam of protons may be insufficient to destroy the cancerous cells within a particular region. In these cases, proton radiation therapy is typically discontinued in favor of other therapies.

SUMMARY OF THE INVENTION

The beam therapy system of the present invention comprises a radiation therapy apparatus which produces beams comprised of two different sub-atomic particles, preferably protons and neutrons. The radiation therapy apparatus is particularly advantageous for treatment of conditions that are unresponsive to proton therapy alone.

In the preferred embodiment, the apparatus comprises a proton beam therapy system and a neutron generator which generates neutrons in response to bombardment by protons. In operation, a proton beam, produced by the proton beam therapy system, is directed toward a target isocenter which is proximate a region of malignant cells. A piece of neutron-rich material, such as Beryllium, is positioned in the path of the proton beam so that at least a portion of the protons collide with atoms within the material and produce neutrons that propagate in the general direction of the path of the proton beam. The apparatus produces a multiple particle beam containing both protons and neutrons which propagates towards the target isocenter in the patient's body. Malignant cells located proximate the target isocenter can thus be bombarded with neutrons alone, protons alone, or both neutrons and protons.

In one embodiment, the plate of a neutron-rich material is interposed between the nozzle of the proton beam therapy system and the patient. As the proton beam passes through the plate, some of the protons collide with atoms in the plate, resulting in the production of neutrons. The nature of the collision causes most of the neutrons to be propelled in the general direction of the proton beam towards the target isocenter in the patient's body.

As is generally understood, the Radio Biologic Effect (RBE) of the neutrons is significantly higher than the Radio Biologic Effect (RBE) of the protons. Hence, the overall effectiveness of the multiple particle beam in damaging the malignant cells can be greater than the overall effectiveness of the proton beam alone.

The number of neutrons that are created by the proton beam passing through the neutron-rich material is dependent, in part, upon the type and thickness of the material. Hence, in one embodiment, plates of different thicknesses can be positioned in an arm that is attached to the nozzle of the proton beam system. In another embodiment, the plate of the neutron-rich material has a varying type or thickness so that the number of neutrons created by the proton beam can be varied by having the proton beam either impinge on different positions on the plate or on different types of plates.

The neutrons emerge from the neutron-rich material with a generally Gaussian distribution. Although the neutrons propagate in the general direction of the proton beam, the neutrons emerging from the neutron-rich plate are not well collimated and, in this sense, there is some beam "spread". Since the neutrons can damage healthy tissue as well as the cancerous or tumorous tissue at the target isocenter, the neutron-rich material is preferably positioned as close to the patient's body as possible to minimize the effect of the beam spread caused by the neutron generation. Preferably, the neutrons represent a small percent of the total radiation dose that is delivered to the patient using the multiple beam therapy system. This relatively low proportion of neutrons to protons further minimizes the collateral damage to the healthy tissue surrounding the target isocenter.

Hence, the preferred embodiment provides a system which can simultaneously or sequentially deliver two different types of particles to a target isocenter within a patient's body thereby producing a heightened Radio Biologic Effect. Implementation can be accomplished inexpensively by modifying an existing proton beam therapy system, i.e., by adding a piece of neutron-rich material in the path of the proton beam.

These and other objects and features of the present invention will become more fully apparent from the following description and appended claims taken in conjunction with the accompanying drawings.

DETAILED DESCRIPTION OF THE PREFERRED EMBODIMENT

Figure 1:
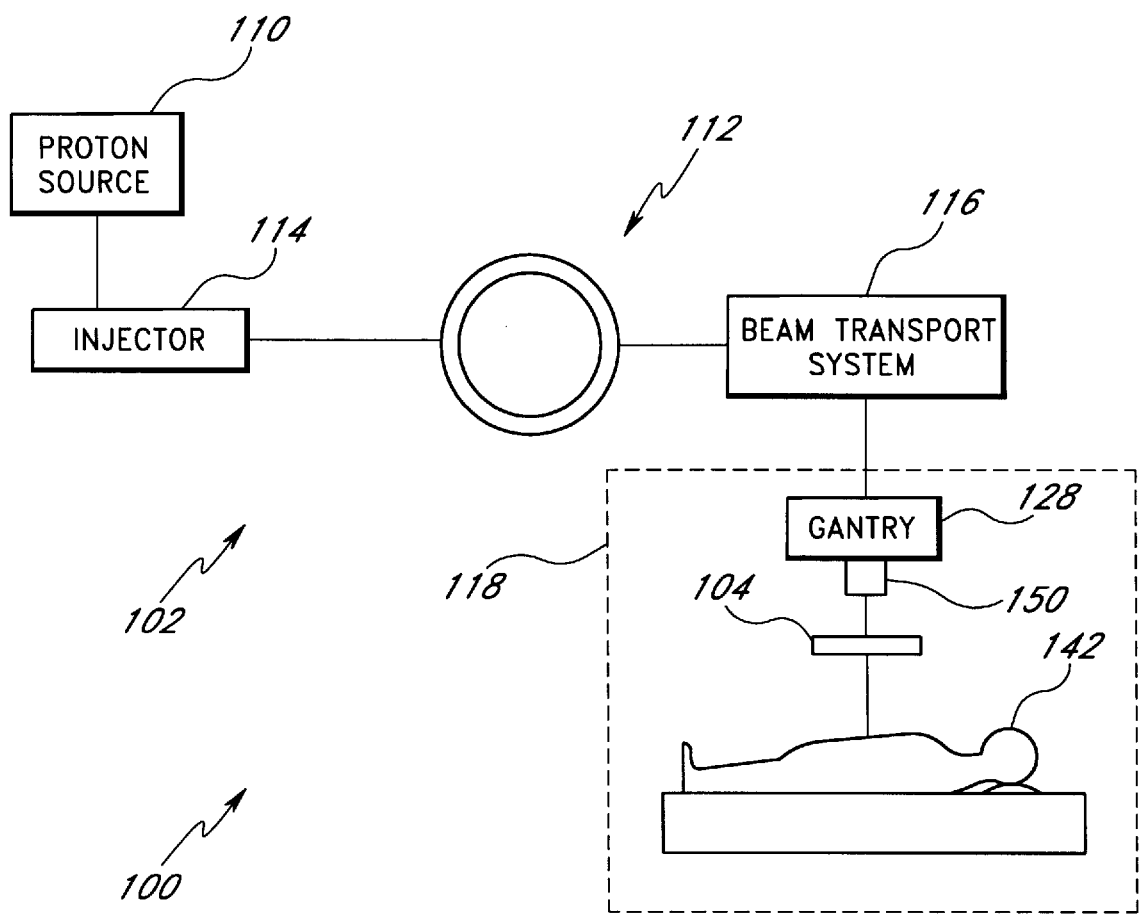
FIG. 1 is a perspective view of a particle beam therapy system of the preferred embodiment.

Reference will now be made to the drawings wherein like numerals refer to like parts throughout. FIG. 1 illustrates a multiple particle beam therapy system 100 which comprises a proton beam therapy system 102 and a neutron source 104. The proton beam therapy system 102 comprises a proton source 110 connected to an accelerator 112 by an injector 114. The accelerator 112 accelerates the protons in a beam to a desired energy level and, via a beam transport system 116, delivers the proton beam to a patient supported in a fixed position at a treatment station 118. The proton therapy system 102 is under operator control via a computer control system (not shown).

At the treatment station 118, a gantry 128 which is rotatable about an axis of rotation supports a patient 142. The beam transport system 116 comprises a nozzle 150 which directs the protons towards a specific target isocenter within the body of a patient. While FIG. 1 illustrates only a single treatment station 118, it can be appreciated that the proton beam therapy system could comprise multiple treatment stations, each having a gantry rotatable about an axis. One embodiment of the proton beam therapy system 102 is more fully described in U.S. Pat. No. 4,870,287 which is hereby incorporated herein by reference.

As is well known in the art, protons are accelerated to a desired energy level in the accelerator 112, which in this preferred embodiment, is comprised of a synchrotron. Magnets are then used to extract the accelerated protons into the beam transport system 116. Switching magnets are used to direct the proton beam through the beam transport system 116 to the treatment station 118 wherein the patient 142 is positioned on a treatment platform 134. The energy level of the protons is preferably selected so that, when the proton beam is directed towards a target isocenter within the patient's body, the Bragg peak of the protons comprising the beam occurs within the region of the target isocenter to maximize the amount of energy delivered to the cells at the target isocenter.

As is understood in the art of proton beam therapy, it is important to deliver the proton beam accurately to the target isocenter. Further, proton beam therapy is generally enhanced when the proton beam can be delivered from a variety of different angles. Hence, it is generally desirable to place the patient 142 in a fixed position relative the nozzle of the beam delivery system 102 and to move the nozzle to various positions via the movable gantry 128 such that the beam is delivered from a variety of different angles. U.S. Pat. No. 4,905,267 and U.S. Pat. No. 5,117,829 each disclose systems for aligning a patient for radiation treatment and each of these references are hereby incorporated herein by reference. Further, U.S. Pat. No. 4,917,334 and U.S. Pat. No. 5,039,057 each disclose a gantry system which allows for delivery of a radiation beam over a continuous range of different angles and each of these patents are hereby incorporated herein by reference. Further, various other methods of selecting treatment for patients, apparatuses for enhancing the delivery of radiation beams to patients, and the like, are disclosed in U.S. Pat. Nos. 5,017,789, 5,240,218 and 5,260,581 which are also hereby incorporated herein by reference.

Figure 2:
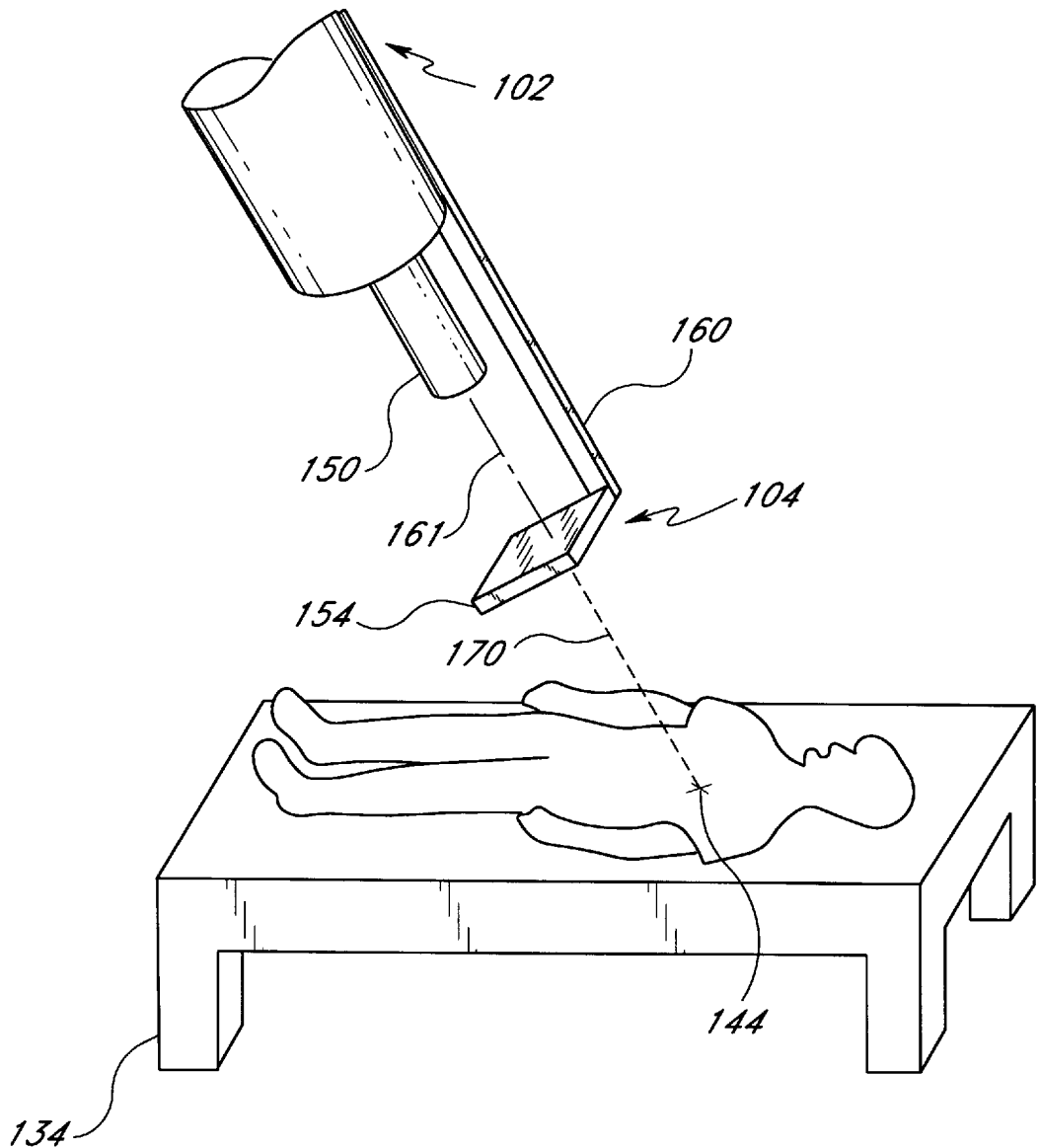
FIG. 2 is a partial schematic view of a treatment station of the particle beam therapy system of the preferred embodiment illustrating the nozzle of a proton beam therapy system with a plate of neutron-rich material for producing neutrons.

FIG. 2 is a schematic illustration of a nozzle 150 of the proton beam therapy system 102 with an attached neutron source 104. In this embodiment, the neutron source 104 is comprised of a piece of neutron-rich material 154 that is coupled to a bracket 160 that is, in turn, mounted on the nozzle 150 so that the neutron-rich material 154 is positioned in the path of a proton beam 161 produced by the proton beam therapy system 102. The neutron source 104 can be positioned in the path of the proton beam 161 to produce neutrons or can alternatively be removed from the path of the proton beam 161 so that the patient only receives protons. Further, the neutron source 104 can be alternatively positioned within and removed from the path of the proton beam 161 so that the patient sequentially receives doses of protons and doses of neutrons as part of a treatment program. When a proton beam 161 impinges upon the neutron-rich material 154, at least a small number of the protons within the beam collide with neutron-rich atoms and cause neutrons to escape from the material 154. As is generally understood, the number of neutrons produced is dependent upon the number of protons within the proton beam, the energy of the protons, the type of the neutron-rich material and the thickness of the neutron-rich material.

In the preferred embodiment, the neutron-rich material 154 is comprised of a plate of Beryllium as this material exhibits the characteristic of having a large number of neutrons that can be generated as a result of a proton beam impinging upon the plate of Beryllium. It can be appreciated, however, that any number of other materials which exhibit this characteristic can be used. The Beryllium plate 154 is detachably mounted to the bracket 160 which allows the operator of the multiple particle beam therapy system 100 to position plates 154 of different thicknesses in front of the proton beam 161 to produce different ratios of neutrons to protons in the multiple particle beam 170. It can also be appreciated that the plate 154 could have varying thicknesses which would allow the operator to vary the ratio of neutrons to protons by simply adjusting the position of the plate 154 relative to the beam as it exits the nozzle 150.

The neutrons generated by the atomic collisions travel in generally the same direction as the proton beam 161. Hence, a multiple particle beam 170 propagates outward from the neutron-rich material 154 towards the patient 142. The protons within the multiple particle beam 170 are still directed and focused towards a target isocenter 144 within the body of the patient 142 so that the protons exhibit the Bragg peak phenomenon at the target isocenter and release a substantial portion of their energy in the proximity of the target isocenter 144. It will be appreciated that the calculations of the desired energy of the proton beam should take into consideration that the beam is travelling through the neutron-rich material in order to have the Bragg peak of the protons occur in the proximity of the desired target isocenter within the patient's body.

Further, the neutron source 104 and the energy and distribution of the proton in the proton beam can be selected so that substantially all of the protons collide with neutrons in the neutron source 104. This will result in the isocenter being bombarded with a beam that is comprised solely of neutrons. Hence, the preferred embodiment discloses a system for producing neutrons for treatment of a patient that is comprised of a neutron source and a proton treatment system.

The neutrons released from the neutron-rich material 154 propagate in a generally Gaussian shaped distribution, in which most of the neutrons are at or near the center of the path of the proton beam 161. Hence, a significant number of neutrons travel towards and through the target isocenter 144 within the body of the patient. These neutrons combine with the protons to destroy or damage tissue containing the malignant cells in the target isocenter 144. It is generally known that the Radio Biologic Effect (RBE) of a neutron is approximately 30–40% greater than the Radio Biologic Effect (RBE) of a proton. Hence, the multiple particle beam 170 produced by the present invention has a higher overall RBE than a proton particle beam alone and can thus be more effective in destroying cells of tumors, cancerous growths, etc.

Due to the destructive potential of neutrons relative to protons, it is generally desirable to limit the total number of neutrons in the multiple particle beam 170 to a small percent, for example, less than 10%, of the total particles within the beam 170 to thereby limit the amount of collateral damage to healthy tissue and cells adjacent the target isocenter 144. It may also be desirable, in some circumstances, to position the plate of neutron-rich material 154 immediately adjacent the entry site of the beam into the patient (e.g., at the patient's skin) to minimize the spread of the neutrons in the multiple particle beam 170.

The foregoing description has involved the production of the neutrons by directing the proton beam through a plate of neutron-rich material. It should be appreciated, however, that the exact manner in which the beams are generated, including the configuration of any neutron-rich material, can be varied without departing from the scope of the present invention.

It can further be appreciated that the exact configuration and composition of the multiple particle beam will be selected on a case by case basis depending upon the type of cells and the position of the cells within the patient's body that are to be targeted. Hence, the actual use of the system will vary depending upon the circumstances surrounding the treatment of the patient.

Although the foregoing description of the preferred embodiment of the present invention has shown, described and pointed out the fundamental novel features of the invention, it will be understood that various omissions, substitutions, and changes in the form of the detail of the apparatus as illustrated, as well as the uses thereof, may be made by those skilled in the art, without departing from the spirit of the present invention. Consequently, the scope of the invention should not be limited to the foregoing discussion, but should be defined by the appended claims.

What is claimed is:

1. A radiation therapy system for treatment of a patient, comprising an apparatus that produces first sub-atomic particles comprising protons and second sub-atomic particles comprising neutrons, said apparatus directing both of said sub-atomic particles towards a selected target location within said patient, wherein said system simultaneously delivers both of said sub-atomic particles towards said selected target location within said patient.

2. The system of claim 1, wherein said apparatus comprises a nozzle which emits at least one of said sub-atomic particles.

3. The system of claim 1, wherein said sub-atomic particles form a beam in which less than about ten percent of the particles in the beam are neutrons.

4. The system of claim 3, wherein said neutrons are produced by a neutron source in response to a portion of said protons colliding with said neutron source.

5. The system of claim 4, wherein said apparatus comprises a nozzle which emits said protons, said neutron source being comprised of a plate of Beryllium interposed between said nozzle and said patient.

6. The system of claim 5, wherein the Beryllium plate has a thickness selected so that said protons colliding with said beryllium plate result in a beam comprised of only neutrons to be produced.

7. The system of claim 1, wherein at least one of said sub-atomic particles is a proton which has an energy level selected so that said proton exhibits a Bragg peak in the proximity of said target location.

8. The system of claim 1, further comprising a gantry for positioning said nozzle in multiple orientations relative to said target location so that sub-atomic particles can be directed towards said target location from each of said multiple orientation of said nozzle.

9. A multiple particle beam therapy system for treating a region of a patient, the region being defined by a target isocenter, comprising:

a proton beam system which produces a beam of protons having a selected energy level wherein said beam of protons emanates out of a nozzle in the direction of a target isocenter within said patient;

a neutron source which can be interposed between said nozzle and said patient and position in the path of said proton beam in a first position wherein said neutron source produces a plurality of neutrons in response to said proton beam impinging upon said neutron source so that a particle beam comprised of both protons and neutrons that travel in the direction of said target isocenter so that both said protons and said neutrons are delivered to the target isocenter within the body of the patient.

10. The system of claim 9, wherein said beam of protons has an energy level which is selected so that said protons in said multiple particle beam exhibit a Bragg peak in the proximity of said target isocenter.

11. The system of claim 10, wherein said neutron source includes a bracket, which is connected to said nozzle of said proton beam system, that holds said piece of neutron-rich material in said first position.

12. The system of claim 9, wherein said proton beam system comprises:

a proton source;

an accelerator which receives protons from said proton source and accelerates said protons to a desired energy level;

a beam transport system for transporting said accelerated protons; and a treatment station which receives said accelerated protons from said beam transport system and directs said accelerated protons out of said nozzle.

13. The system of claim 9, wherein said proton beam system includes a gantry system which allows said nozzle to rotate about an axis so that said proton beam emanates out of said nozzle toward said target isocenter from a plurality of different rotational orientations relative said target isocenter.

14. The system of claim 13, wherein said neutron source is attached to said nozzle so that said neutron source remains in said first position relative said nozzle interposed between said nozzle and said patient as said nozzle is moved to different rotational orientations relative said target isocenter.

15. The system of claim 14, wherein said neutron source is movable relative said nozzle.

16. The system of claim 14, wherein said piece of neutron-rich material comprises a piece of Beryllium.

17. The system of claim 14, wherein said piece of neutron-rich material has a pre-selected thickness value wherein said pre-selected thickness value is selected so that said multiple particle beam is produced which has a desired ratio of neutrons to protons.

18. The system of claim 17, wherein said multiple particle beam comprises less than 10% neutrons.

19. The system of claim 18, wherein said piece of neutron-rich material has a plurality of sections with different thickness values so that a different ratio of neutrons to protons can be obtained for said multiple particle beam by said proton beam impinging on a different section of said piece of neutron-rich material.

20. The system of claim 18, wherein said protons in said multiple particle beam travel toward said target isocenter and exhibit a Bragg peak in proximity of said target isocenter.

21. The system of claim 20, wherein said neutrons in said multiple particle beam emanate from said neutron-rich material in a generally Gaussian distribution travelling in the general direction of said target isocenter.

22. The system of claim 21, wherein said first position is located immediately adjacent said patient so that said neutrons travel through said patient's body in a region which is substantially adjacent said target isocenter.

23. The system of claim 9, wherein said neutron source is comprised of a piece of neutron-rich material positioned in said first position so that said beam of proton impinges on said neutron-rich material and wherein a portion of said protons comprising said proton beam collide with atoms comprising said neutron-rich material thereby causing neutrons to be released from said neutron-rich material so that said multiple particle beam is formed.

24. A method of radiation therapy comprising the step of directing energy comprised of at least two types of sub-atomic particles towards a common target within a patient, wherein the step of directing energy comprises producing a mixed beam comprised of proton and neutron particles so that said two types of particles are delivered to the common target within the patient simultaneously.

25. The method of claim 24, wherein the step of directing comprises limiting the mixed beam to less than 10% neutrons.

26. method of claim 25, wherein the directing step comprises the steps of:

producing a beam of protons;

directing said beam of protons towards a neutron source so that a portion of the protons in said beam of protons collide with said neutron source and cause neutrons to emanate out of said neutron source.

27. The method of claim 26, wherein said neutron source is comprised of a plate of neutron rich material.

28. The method of claim 27, wherein said plate of neutron rich material is comprised of a plate of Beryllium.

29. A method of treating cells in the proximity of a target isocenter located within a patient's body comprising the steps of:

producing a beam of protons having a pre-selected energy level; and directing said beam of protons at a neutron source so that a multiple particle beam, comprised of protons and neutrons, is generated wherein said multiple particle beam propagates toward said target isocenter so that said target isocenter is irradiated by both said protons and neutrons comprising said multiple particle beam.

30. The method of claim 29, wherein said step of producing a beam of protons comprises the steps of:

generating a plurality of protons;

accelerating said plurality of protons to a desired energy level; and directing said accelerating plurality of protron to a nozzle so that said plurality of protons exit said nozzle as said proton beam.

31. The method of claim 30, wherein said step of generating said multiple particle beam comprises:

positioning a piece of neutron-rich material in a first position between said nozzle and said target isocenter in said patient; and directing said proton beam so that said beam impinges on said piece of neutron-rich material, wherein a portion of said proton in said proton beam collide with the atoms comprising said piece of neutron-rich material causing neutrons to emanate from said piece of neutron-rich material in the direction of said target isocenter.

32. The method of claim 31, wherein said step of positioning a piece of neutron-rich material in a first position comprises:

mounting a bracket to said nozzle; and mounting a piece of Beryllium on said bracket so that said piece of Beryllium is substantially adjacent said patient in said first position.

33. The method of claim 32, wherein said protons in said beam exhibit a Bragg peak in the proximity of said target isocenter.

* * * * *